United States Patent
Tajima et al.

(10) Patent No.: US 11,642,505 B2
(45) Date of Patent: May 9, 2023

(54) APPLICATOR, CARTRIDGE AND APPLICATION KIT

(71) Applicant: HISAMITSU PHARMACEUTICAL CO., INC., Tosu (JP)

(72) Inventors: Takuya Tajima, Tsukuba (JP); Naoki Yamamoto, Tsukuba (JP); Seiji Tokumoto, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 457 days.

(21) Appl. No.: 16/767,290

(22) PCT Filed: Nov. 6, 2018

(86) PCT No.: PCT/JP2018/041241
§ 371 (c)(1),
(2) Date: May 27, 2020

(87) PCT Pub. No.: WO2019/107092
PCT Pub. Date: Jun. 6, 2019

(65) Prior Publication Data
US 2020/0316355 A1 Oct. 8, 2020

(30) Foreign Application Priority Data
Nov. 30, 2017 (JP) .............................. JP2017-230459

(51) Int. Cl.
*A61M 37/00* (2006.01)

(52) U.S. Cl.
CPC . *A61M 37/0015* (2013.01); *A61M 2205/0216* (2013.01)

(58) Field of Classification Search
CPC ...... A61M 37/0015; A61M 2205/0216; A61M 2037/0023; A61M 37/00;
(Continued)

(56) References Cited

U.S. PATENT DOCUMENTS

| 2013/0226098 A1 | 8/2013 | Tokumoto et al. |
| 2016/0354589 A1 | 12/2016 | Kobayashi et al. |

FOREIGN PATENT DOCUMENTS

| CN | 101208130 A | 6/2008 |
| CN | 103687643 A | 3/2014 |

(Continued)

OTHER PUBLICATIONS

Taiwanese Office Action dated Aug. 25, 2020 corresponding to Patent Application No. 107141888.
(Continued)

*Primary Examiner* — Amber R Stiles
(74) *Attorney, Agent, or Firm* — Nath, Goldberg & Meyer; Joshua B. Goldberg

(57) ABSTRACT

An application kit according to one embodiment includes: a cartridge including a sheet member; and an applicator being connectable to the cartridge. The cartridge includes a bending portion configured to bend the sheet member and a cartridge-side connector configured to be detachably connected to the applicator. The applicator includes: an applicator body; an applicator-side connector provided to a bottom portion of the applicator body; a cap provided above the applicator body and being movable along a height direction of the applicator body; and an elastic member extending along the height direction between the applicator body and the cap and configured to apply, to the cap, an elastic force that acts in a direction away from the bottom portion.

13 Claims, 13 Drawing Sheets

(58) Field of Classification Search
CPC ... A61M 2037/0061; A61M 2205/0244; A61F 13/00063; A61F 13/00085
See application file for complete search history.

(56) References Cited

FOREIGN PATENT DOCUMENTS

| | | |
|---|---|---|
| CN | 105324148 A | 2/2016 |
| CN | 105555353 A | 5/2016 |
| CN | 106456954 A | 2/2017 |
| CN | 106999702 A | 8/2017 |
| EP | 1360935 A1 | 11/2003 |
| JP | 2008543528 A | 12/2008 |
| JP | 2014200979 A | 10/2014 |
| KR | 10-2011-0138685 A | 12/2011 |
| KR | 10-2017-0093809 A | 8/2017 |
| WO | 0202177 A1 | 1/2002 |
| WO | 2007002522 A1 | 1/2007 |
| WO | 2009142741 A1 | 11/2009 |
| WO | 2013187392 A1 | 12/2013 |
| WO | 2014097837 A1 | 6/2014 |
| WO | 2016088886 A1 | 6/2016 |
| WO | WO-2016088886 A1 * | 6/2016 ........... A61K 9/0021 |
| WO | 2016129184 A1 | 8/2016 |
| WO | 2017038499 A1 | 3/2017 |
| WO | 2017135474 A1 | 8/2017 |
| WO | 2017145891 A1 | 8/2017 |
| WO | 2017189259 A2 | 11/2017 |
| WO | 2018116990 A1 | 6/2018 |

OTHER PUBLICATIONS

Chinese Office Action dated Jul. 5, 2021 corresponding to application No. 201880076512.2.
European Search Report dated Aug. 2, 2021 corresponding to application No. 18884522.6.
Korean Office Action dated May 27, 2021 corresponding to application No. 10-2020-7013303.
International Search Report dated Dec. 4, 2018 corresponding to application No. PCT/JP2018/041241.
International Preliminary Report on Patentability dated Jun. 11, 2020 corresponding to application No. PCT/JP2018/041241.

* cited by examiner

APPLICATOR, CARTRIDGE AND APPLICATION KIT

This is a National Phase Application filed under 35 U.S.C. 371 as a national stage of PCT/JP2018/041241, filed Nov. 6, 2018, an application claiming the benefit of Japanese Application No. 2017-230459, filed Nov. 30, 2017, the content of each of which is hereby incorporated by reference in its entirety.

TECHNICAL FIELD

One aspect of the present invention relates to an applicator, a cartridge, and an application kit used for assisting administration of an active ingredient.

Background Art

Conventionally, sheet members for administering an active ingredient through skin have been known. Examples of the sheet members include a patch described in Patent Literature 1 below and a microneedle sheet described in Patent Literature 2 below.

CITATION LIST

Patent Literature

[Patent Literature 1] WO 2002/002177
[Patent Literature 2] WO 2013/187392

SUMMARY OF INVENTION

Technical Problem

A user sticks or attaches a sheet member to his/her skin by hand or using some auxiliary tool, thereby applying the sheet member to the skin. However, because force applied when such a sheet member is applied to skin varies depending on individual users, the condition for applying the sheet member accordingly varies among users, and consequently variations may occur in administration of an active ingredient. In view of this, it is desired to reduce variations in application of a sheet member to skin.

Solution to Problem

An applicator according to one aspect of the present invention includes: an applicator body; an applicator-side connector provided to a bottom portion of the applicator body and configured to be detachably connected to a cartridge including a bending portion configured to bend a sheet member for applying the sheet member to skin; a cap provided above the applicator body and being movable along a height direction of the applicator body; and an elastic member extending along the height direction between the applicator body and the cap and configured to apply, to the cap, an elastic force that acts in a direction away from the bottom portion. In a pressed state in which the applicator-side connector has been connected to the cartridge and the cap has been moved toward the bottom portion against the elastic force, the bending portion bends the sheet member that has advanced to the bending portion.

A cartridge according to one aspect of the present invention includes: a sheet member; a bending portion configured to bend the sheet member for applying the sheet member to skin; and a cartridge-side connector configured to be detachably connected to an applicator configured to apply a force toward the sheet member. In a pressed state in which the cartridge-side connector has been connected to the applicator and the applicator has applied the force to the cartridge, the bending portion bends the sheet member that has advanced to the bending portion.

An application kit according to one aspect of the present invention includes: a cartridge including a sheet member; and an applicator being connectable to the cartridge. The cartridge includes: a bending portion configured to bend the sheet member for applying the sheet member to skin; and a cartridge-side connector configured to be detachably connected to the applicator. The applicator includes: an applicator body; an applicator-side connector provided to a bottom portion of the applicator body; a cap provided above the applicator body and being movable along a height direction of the applicator body; and an elastic member extending along the height direction between the applicator body and the cap and configured to apply, to the cap, an elastic force that acts in a direction away from the bottom portion. In a pressed state in which the cartridge-side connector has been connected to the applicator-side connector and the cap has been moved toward the bottom portion against the elastic force, the bending portion bends the sheet member that has advanced to the bending portion.

In these aspects, the sheet member is bent by the bending portion and is applied to the skin in the pressed state in which the applicator has been connected to the cartridge and the cap has been moved toward the bottom portion. By this mechanism, whoever uses this applicator, the sheet member is applied to the skin with a certain or greater pressing force being applied to the sheet member from the applicator via the cartridge. Because the pressing force applied to the sheet member is maintained at a certain or greater level during the application, variations in application of the sheet member to the skin can be reduced.

Advantageous Effects of Invention

According to each aspect of the present invention, variations in application of the sheet member to the skin can be reduced.

DESCRIPTION OF EMBODIMENTS

An embodiment of the present invention will now be described in detail with reference to the attached drawings. In the description of the drawings, like or equivalent elements are designated by like reference signs, and duplicated explanation is omitted.

[Overview of Application Kit]

An application kit is an auxiliary tool used when a sheet member for administering any active ingredient (e.g., a pharmaceutical substance) into a living body is applied to skin. When using the application kit, a user can apply the sheet member to his/her skin with force that is more appropriate than when applying the sheet member directly by hand. The expression "the sheet member is applied to skin" at least means that the sheet member is in contact with the skin. The sheet member has a planar shape, and is flexible so as to be folded back or follow a surface profile of skin. The sheet member is not limited to a particular one, and examples thereof include a patch and a microneedle sheet. In the present embodiment, a microneedle sheet will be described as one example of the sheet member.

[Microneedle Sheet]

Figure 1:
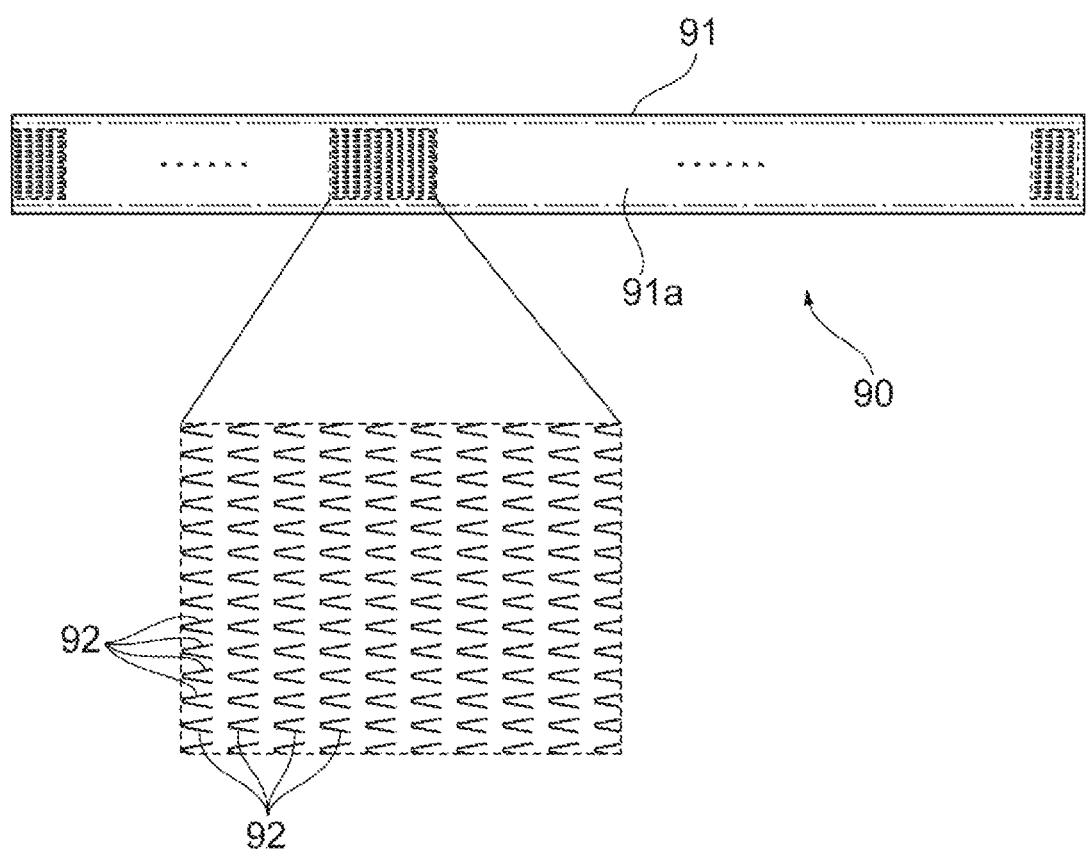
FIG. 1 is a plan view of a microneedle sheet used together with an application kit according to an embodiment.

Referring to FIG. 1, the following describes a microneedle sheet 90 used together with an application kit according to the embodiment. FIG. 1 is a plan view of the microneedle sheet 90. As illustrated in this diagram, the microneedle sheet 90 has a belt (elongated rectangular) shape. The microneedle sheet 90 has a sheet body 91 and a plurality of microneedles 92 formed on the sheet body 91. In the present embodiment, the direction along a long side of the microneedle sheet 90 (or the sheet body 91) is called the longitudinal direction of the microneedle sheet 90 (or the sheet body 91), and the direction along a short side (direction orthogonal to the longitudinal direction) of the microneedle sheet 90 (or the sheet body 91) is called the width direction of the microneedle sheet 90 (or the sheet body 91). The direction orthogonal to both the longitudinal direction and the width direction is called the thickness direction of the microneedle sheet 90 (or the sheet body 91).

The thickness (length along the thickness direction) of each microneedle 92 is the same as the thickness of the sheet body 91. The microneedles 92 are formed such that two or more microneedles 92 are aligned in both the longitudinal direction and the width direction of the sheet body 91. At the time when the microneedle sheet 90 is provided for use, each microneedle 92 does not rise from a main surface 91a of the sheet body 91 and is in a state of lying along the main surface 91a. In other words, the tips of the respective microneedles 92 are oriented toward one end of the sheet body 91 in the longitudinal direction (to the left in FIG. 1). This can also be translated into that the angle formed by each microneedle 92 and the sheet body 91 is 0 degrees or about 0 degrees. The orientation of the tip of each microneedle 92 corresponds to the direction in which the microneedle sheet 90 advances when the microneedle sheet 90 is used. The orientation of some of the microneedles 92 may be different from the orientation of the other microneedles 92.

Material for the microneedle sheet 90 and the microneedles 92 is not limited to a particular one. For example, the microneedle sheet 90 and the microneedles 92 may be made of any of stainless steel, poly(ethylene terephthalate) (PET), water-soluble polymers, other metals, other resins, biodegradable material, ceramic, and bioabsorbable material. Alternatively, the microneedle sheet 90 and the microneedles 92 may be made of these materials in combination.

The microneedles 92 can be formed by etching. When the sheet is metal, the microneedles 92 can be formed by partially dissolving the sheet with a chemical solution. When the sheet is nonmetal, the microneedles 92 can be formed by partially cutting the sheet with a laser. In these cases, a void is formed around each microneedle 92. As a matter of course, the microneedles 92 may be formed by a method other than laser processing and etching. In all of these cases, the microneedles 92 do not have to be raised from the main surface 91a of the sheet in advance, and thus the microneedle sheet 90 can be produced easily at low cost.

In the present embodiment, each microneedle 92 has a triangular shape. However, the shape of the microneedle is not limited to a particular one. Although the size and orientation of the microneedles 92 are uniform in the example in FIG. 1, at least one of the size and orientation thereof does not have to be uniform. When each microneedle 92 has a triangular shape, the lower limit of the angle of its tip portion may be 10 degrees or 20 degrees, for example, and the upper limit of the angle thereof may be 150 degrees or 120 degrees, for example. The distribution of the microneedles 92 in the microneedle sheet 90 may or may not be uniform. For example, when the microneedle sheet 90 is viewed along the longitudinal direction, a plurality of microneedles 92 may be formed on the sheet body 91 such that areas containing one or more microneedles 92 and areas containing no microneedles 92 are alternately arranged.

The dimensions of the microneedle sheet 90 are also not limited to particular ones. Specifically, the lower limit of thickness may be either 5 micrometers or 20 micrometers, and the upper limit of the thickness may be either 1000 micrometers or 300 micrometers. The lower limit of length may be either 0.1 centimeter or 1 centimeter, and the upper limit of the length may be 50 centimeters or 20 centimeters. The lower limit of width may be either 0.1 centimeter or 1 centimeter, and the upper limit of the width may be either 60 centimeters or 30 centimeters. The lower limits of length and width of the microneedle sheet 90 are determined in consideration of the amount of an active ingredient to be administered, and the upper limits of length and width thereof are determined in consideration of the size of a living body.

Parameters for the microneedles 92 are also not limited to particular ones. Specifically, the lower limit of needle height may be 10 micrometers or 100 micrometers, and the upper limit of the height may be 10000 micrometers, 1000 micrometers, or 500 micrometers. The lower limit of needle density may be 0.05 needle/cm$^2$ or 1 needle/cm$^2$, and the upper limit of the density may be 10000 needles/cm$^2$ or 5000 needles/cm$^2$. The lower limit of the density is a value calculated based on the number of needles and the area that enable administration of 1 milligram of an active ingredient, and the upper limit of the density is a limit value determined in consideration of the shape of each needle.

Examples of a method considered for preparing an active ingredient to be applied to skin include: a method of causing the microneedle sheet 90 itself (more specifically, the microneedles 92 themselves) to contain the active ingredient in advance; a method of coating the microneedle sheet 90 itself with the active ingredient in advance; a method of applying the active ingredient onto skin before the skin is punctured with the microneedles 92; and a method of applying the active ingredient onto skin after the skin is punctured with the microneedles 92. If the microneedle sheet 90 is coated with the active ingredient in advance, coating liquid having a predetermined viscosity is preferably applied in uniform thickness to the entire sheet. Such uniform application can be easily performed because the tips of the microneedles 92 are oriented toward the one end of the sheet body 91 (because the microneedles 92 lie along the main surface 91*a*). This coating may be performed by using a principle of screen printing, or may be performed by using another method. The microneedle sheet 90 itself can contain the active ingredient, for example, when a biodegradable sheet or a sheet made with water-soluble polymer is used.

The microneedle sheet 90 may be provided in such a form that the main surface 91*a* is protected by a release liner. Examples of material of the release liner include plastics such as PET. However, the material is not limited to a particular one, and the release liner may be made with metal and another type of resin, for example. The microneedle sheet 90 is fixed or temporarily attached to one side of this release liner with a tape or adhesive, for example.

The respective microneedles 92 are in a state of lying along the main surface 91*a* of the sheet body 91 before being bent by the application kit. Thus, unless the application kit is used, there is no need to worry that the microneedles 92 may come into contact with or be caught in another object (e.g., skin or clothes of a user). Consequently, safety from the microneedles 92 when being handled can be obtained. For example, the user can safely perform storage and transfer of the microneedle sheet 90, and preparation thereof immediately before using it.

[Configuration of Application Kit]

Figure 2:
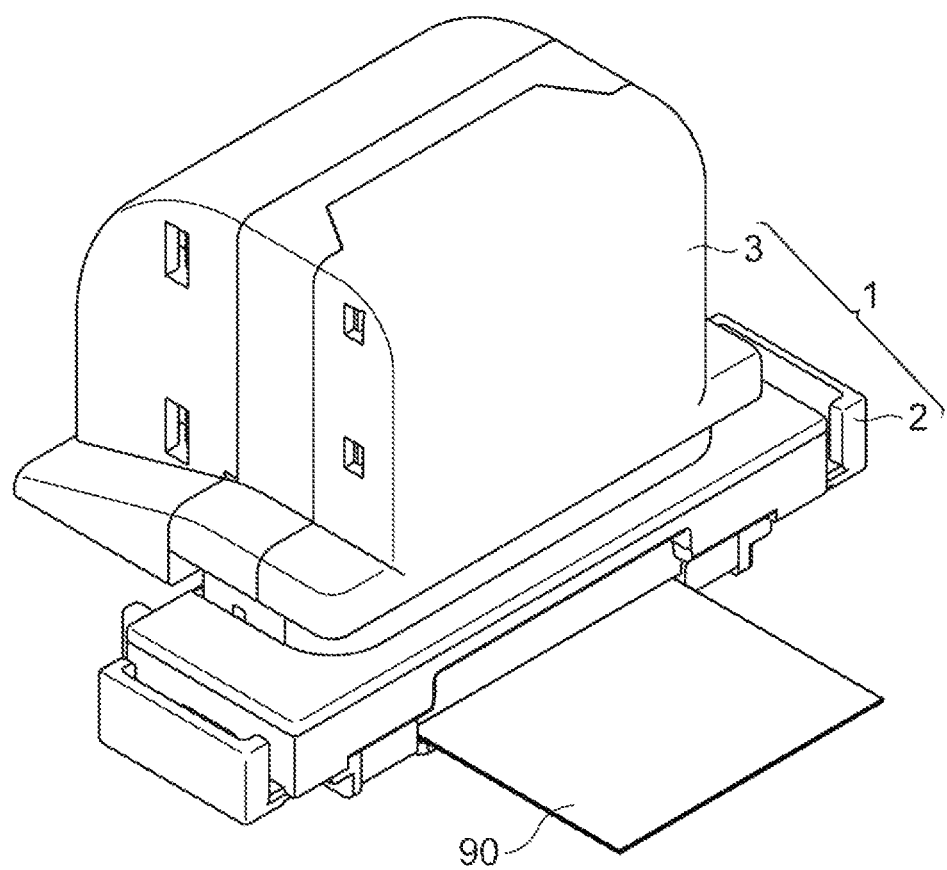
FIG. 2 is a perspective view of the application kit according to the embodiment when viewed from above.
Figure 3:
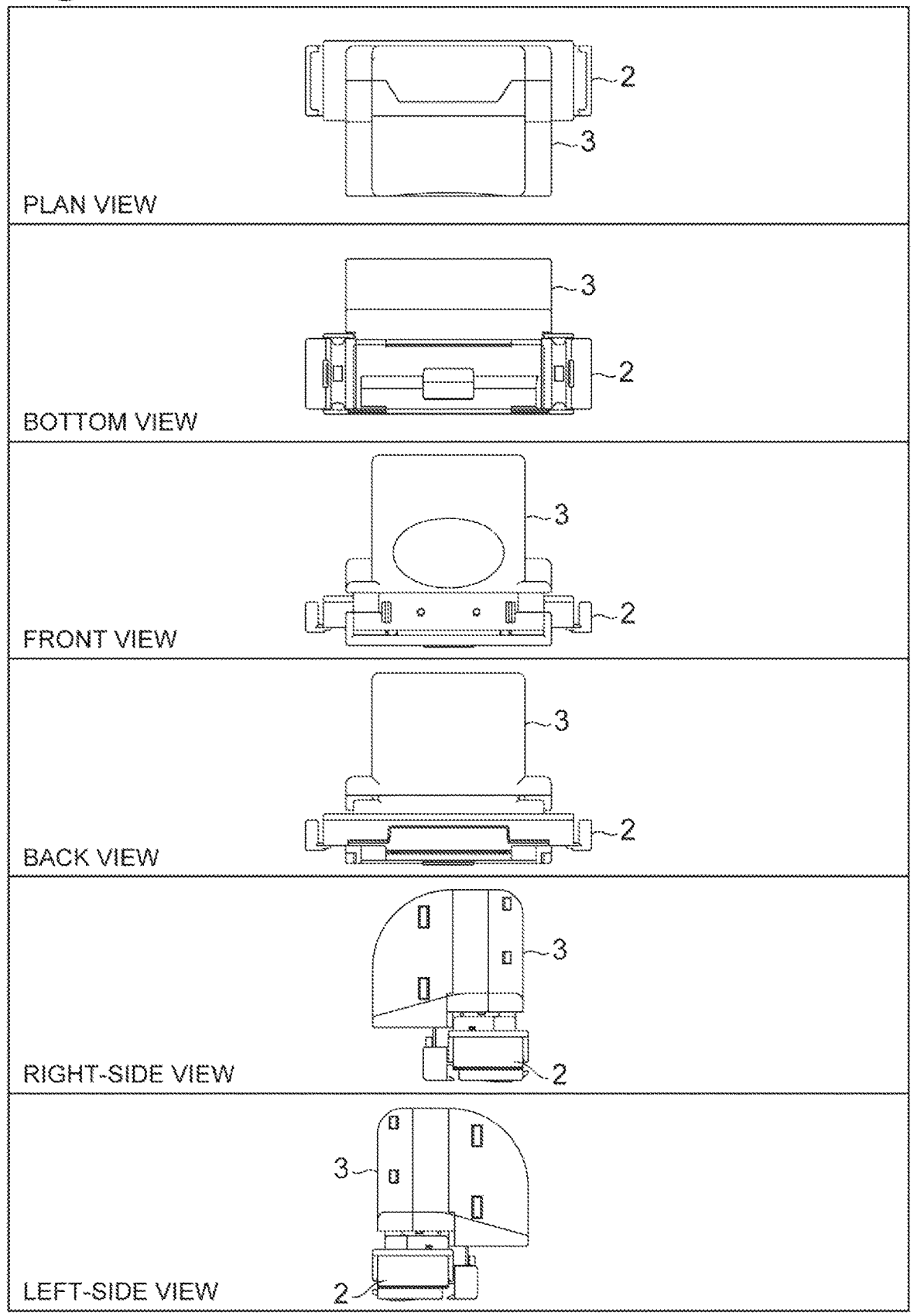
FIG. 3 is a six-sided view of the application kit according to the embodiment.

FIG. 2 is a perspective view of an application kit 1 according to the embodiment when viewed from above. FIG. 3 is a six-sided view of the application kit 1. In FIG. 3, the microneedle sheet 90 is omitted. The application kit 1 includes a cartridge 2 including the microneedle sheet 90 (sheet member) and an applicator 3 being connectable to the cartridge 2. When the user has attached the cartridge 2 to a bottom portion of the applicator 3, a set of the cartridge 2 and the applicator 3 serves as the application kit 1. The user moves this application kit 1 on his/her skin to apply the microneedle sheet 90 to the skin. After application of the microneedle sheet 90 has been completed, the user can apply another new microneedle sheet 90 to the skin by removing the cartridge 2 from the applicator 3 and then attaching a new cartridge 2 to the applicator 3. In this manner, the applicator 3 is a tool that can be used repeatedly. In contrast, the cartridge 2 is a disposable tool.

In the present embodiment, the side closer to the applicator 3 is defined as the upper side of the application kit 1, and the side closer to the cartridge 2 is defined as the lower side of the application kit 1. The side on which the microneedle sheet 90 enters the cartridge 2 when the application kit 1 is used is defined as the rear side of the application kit 1, and the side opposite thereto is defined as the front side of the application kit 1. The direction orthogonal to both the vertical direction and the front-and-rear direction of the application kit 1 is defined as the width direction of the application kit 1. The directions thus defined are used also in descriptions of the applicator 3 as a single component and the cartridge 2 as a single component. In FIG. 2, illustration is provided such that the rear side of the application kit 1 is positioned on the near side.

[Configuration of Cartridge]

Figure 4:
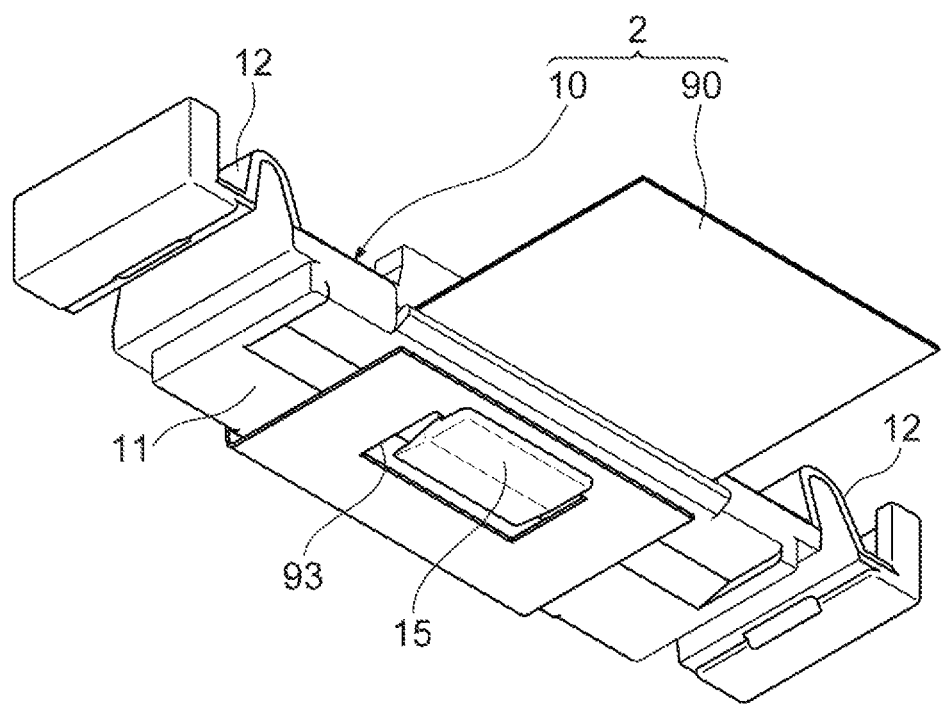
FIG. 4 is a perspective view of a cartridge according to the embodiment when viewed from below.
Figure 5:
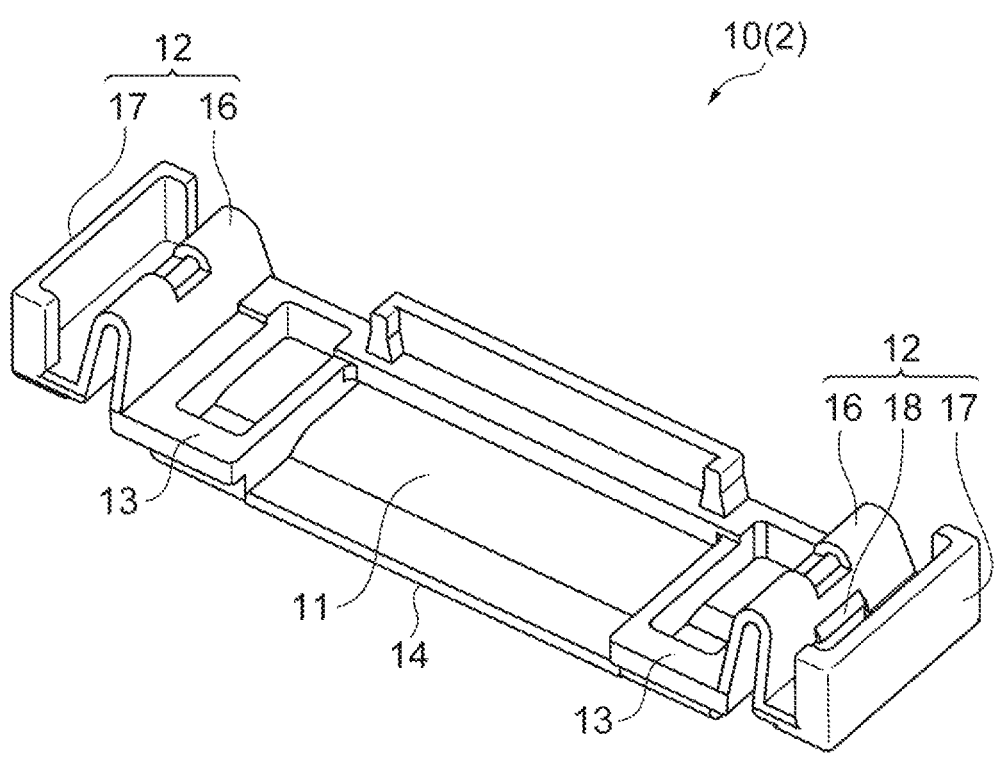
FIG. 5 is a perspective view of the cartridge according to the embodiment when viewed from above.
Figure 6:
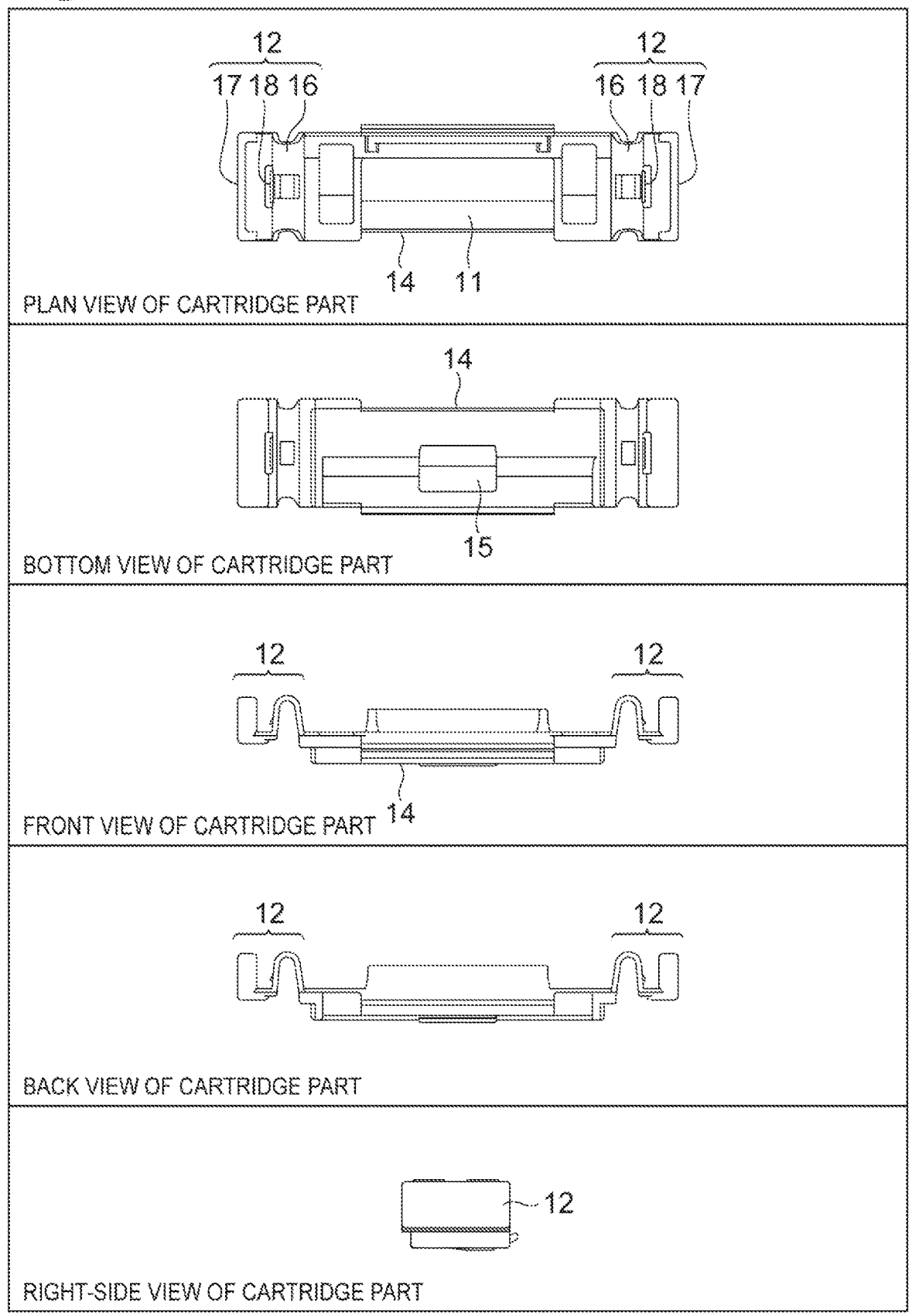
FIG. 6 is a six-sided view of the cartridge according to the embodiment.

FIG. 4 is a perspective view of the cartridge 2 when viewed from below, and FIG. 5 is a perspective view of the cartridge 2 when viewed from above. FIG. 6 is a six-sided view of the cartridge 2. In FIG. 5 and FIG. 6, the microneedle sheet 90 is omitted. In FIG. 6, the left-side view symmetrical to the right-side view is omitted. The cartridge 2 includes a microneedle sheet 90 (sheet member) and a cartridge body 10 configured to support the microneedle sheet 90. The microneedle sheet 90 is attached to the cartridge body 10, whereby the cartridge 2 is formed.

The cartridge body 10 is a small component having a structure corresponding to the bottom portion of the applicator 3 (more specifically, a bottom portion of an applicator body 20). The cartridge body 10 includes a support plate 11 and a pair of cartridge-side connectors 12.

The support plate 11 is a rectangular plate configured to support at least part of the microneedle sheet 90. The width of an upper surface of the support plate 11 is set according to the width of the microneedle sheet 90, and this setting allows the microneedle sheet 90 before being applied to skin to advance straight forward without wobbling. In the present embodiment, guides 13 are provided in order to define the width of the upper surface of the support plate 11.

The cartridge body 10 includes a linear bending portion 14 configured to bend the microneedle sheet 90 that has advanced to the bending portion 14 to apply the microneedle sheet 90 to skin. The width of the bending portion 14 is set so as to correspond to the width of the microneedle sheet 90. In the present embodiment, the bending portion 14 is a front end (a linear edge on the front side) of the support plate 11. However, the specific shape or structure of the bending portion 14 is not limited to a particular one. For example, the bending portion 14 may be formed with an elongated columnar member.

On a lower surface of the support plate 11, a claw 15 for fixing a first end of the microneedle sheet 90 in the longitudinal direction to the cartridge 2 is formed. A through hole 93 corresponding to the claw 15 is formed near the first end of the microneedle sheet 90. The microneedle sheet 90 is attached to the cartridge body 10 in advance by placing the first end of the microneedle sheet 90 onto the upper surface of the support plate 11, pulling out the first end to the bending portion 14, bending the microneedle sheet 90 with the bending portion 14, and hooking, on the claw 15, the through hole 93 that has been moved to the lower surface of the support plate 11. In order to more reliably attach the microneedle sheet 90 to the cartridge body 10, an area near the first end of the microneedle sheet 90 may be fixed to the lower surface of the cartridge body 10 with adhesive or glue. When the main surface 91*a* of the microneedle sheet 90 is protected by a release liner, the microneedle sheet 90 is placed on the upper surface of the support plate 11 with this release liner facing upward. When the application kit 1 is used, the release liner is peeled from the sheet body 91 near the bending portion 14, and the main surface 91*a* of the microneedle sheet 90 bent by the bending portion 14 faces the skin.

The pair of cartridge-side connectors 12 are portions configured to be detachably connected to the applicator 3, and are provided to both ends of the support plate 11 in the width direction. Each cartridge-side connector 12 has an N-shape or an inverse N-shape when the cartridge body 10 is viewed along the front-and-rear direction. Specifically, each cartridge-side connector 12 has a fitting portion 16 having an inverse U-shape and formed on an end portion of the support plate 11 and a handle 17 formed outside the fitting portion 16 in the width direction. On an outer wall of the fitting portion 16, a claw 18 is formed.

[Configuration of Applicator]

Figure 7:
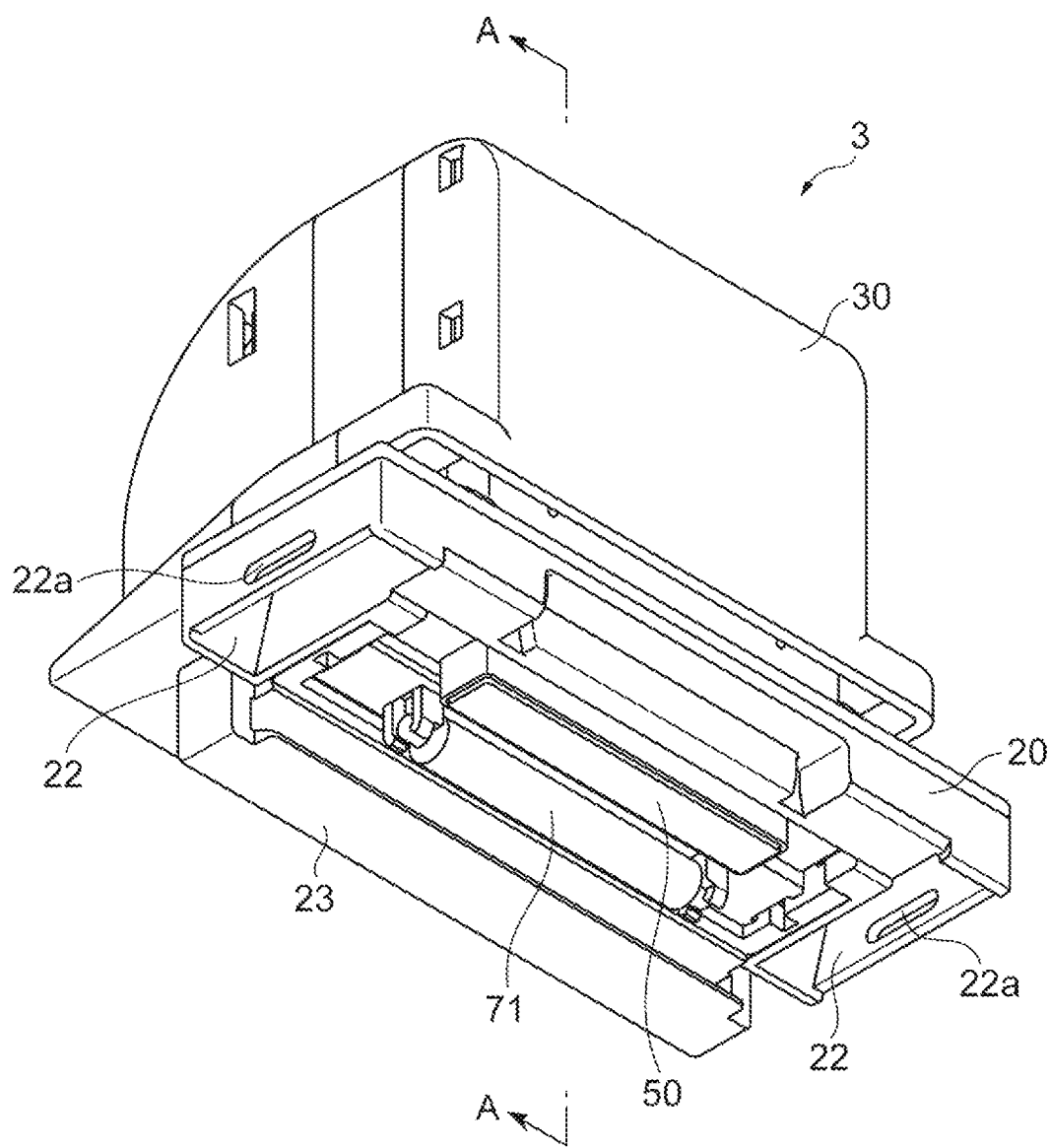
FIG. 7 is a perspective view of an applicator according to the embodiment when viewed from below.
Figure 8:
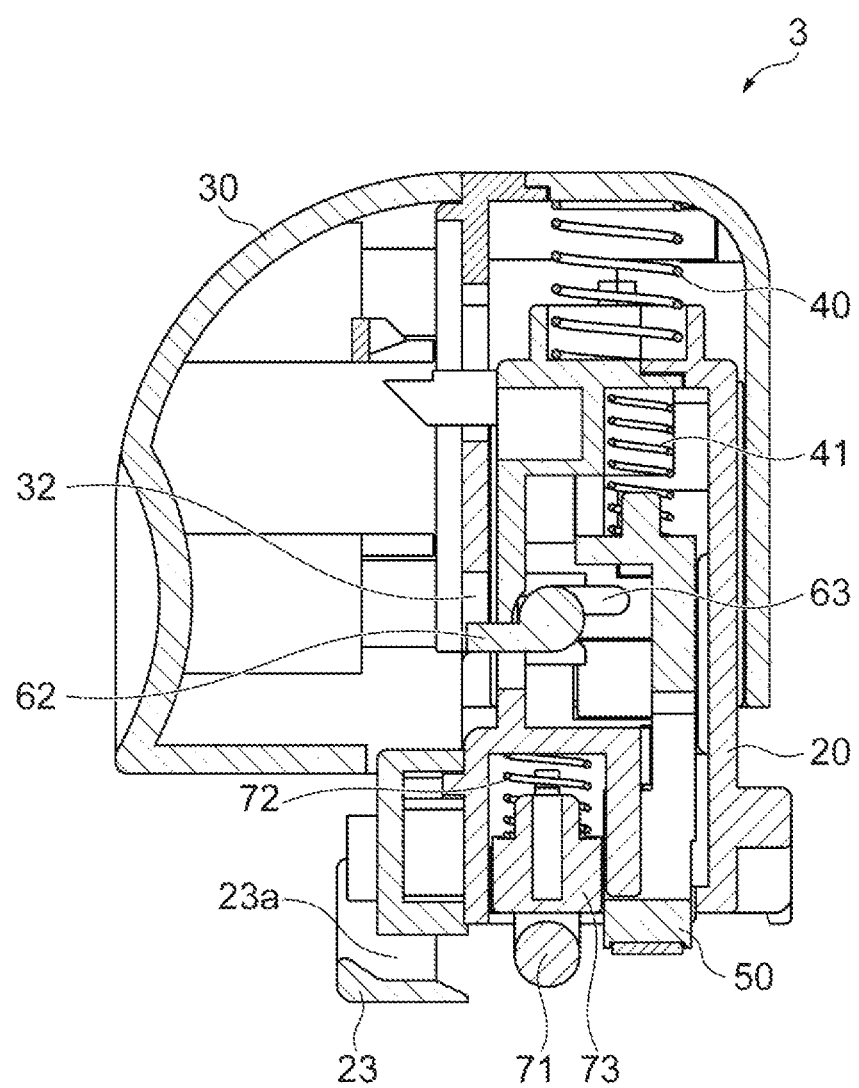
FIG. 8 is a sectional view of FIG. 7 taken along line A-A.
Figure 9:
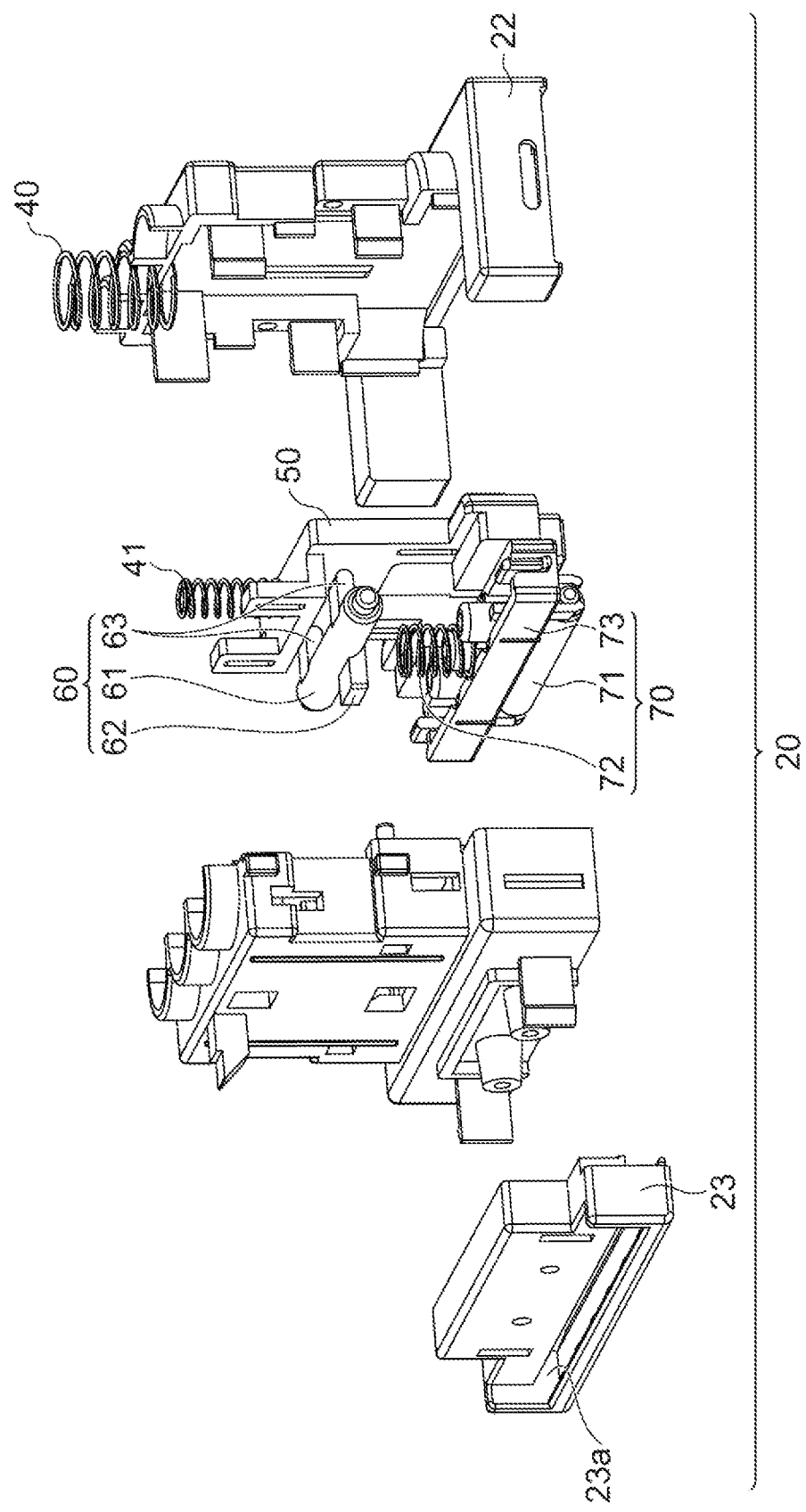
FIG. 9 is an exploded perspective view illustrating an internal structure of the applicator according to the embodiment.
Figure 10:
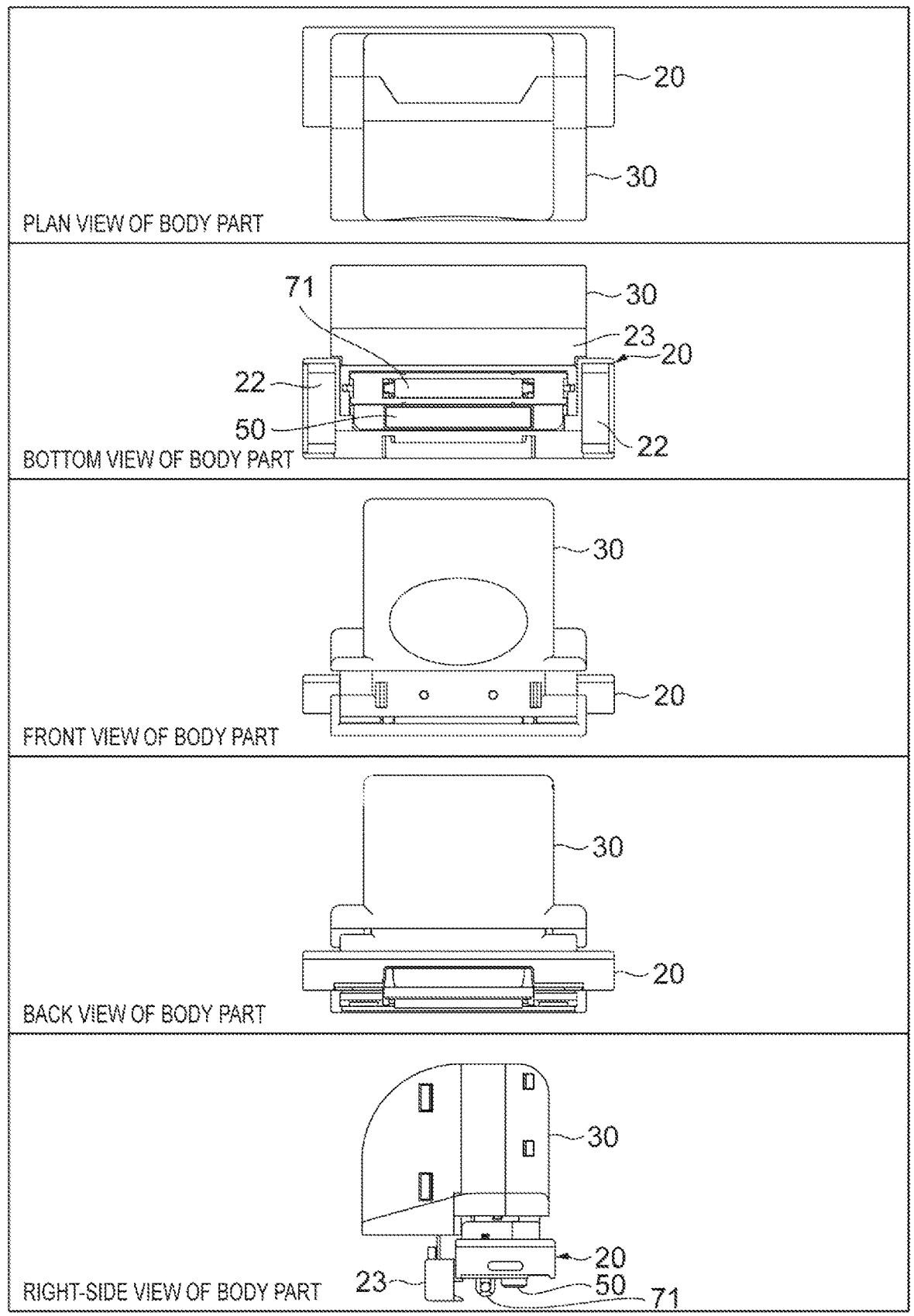
FIG. 10 is a six-sided view of the applicator according to the embodiment.

FIG. 7 is a perspective view of the applicator 3 when viewed from below, and FIG. 8 is a sectional view of FIG. 7 taken along line A-A. FIG. 9 is an exploded perspective view illustrating an inner structure (applicator body 20) of the applicator 3. FIG. 10 is a six-sided view of the applicator 3. In FIG. 10, the left-side view symmetrical to the right-side view is omitted. The applicator 3 includes: the applicator body 20 having a rectangular parallelepiped shape that is vertically long; and a cap 30 that is attached to the applicator body 20 so as to cover a top portion of the applicator body 20. The cap 30 can be moved along the height direction of the applicator body 20. Specifically, the cap 30 can be moved along the height direction toward the bottom portion of the applicator body 20 or in a direction away from the bottom portion.

The movement of the cap 30 with respect to the applicator body 20 is controlled with a compression spring 40 extending along the height direction between the applicator body 20 and the cap 30. The compression spring 40 is one example of an elastic member configured to apply, to the cap 30, elastic force acting in the direction away from the bottom portion thereby controlling the movement of the cap 30 with respect to the applicator body 20. In the present embodiment, the compression spring 40 is a linear coil spring. However, the type of the compression spring is not limited to this, and a nonlinear coil spring, for example, may be used instead. In the present embodiment, one end of the compression spring 40 is attached to the upper surface of the applicator body 20, and the other end thereof is attached to the ceiling of the cap 30. If the compression spring 40 can apply, to the cap 30, elastic force acting in the direction away from the bottom portion, the specific position where the compression spring 40 (elastic member) is attached is not limited to a particular one. For example, one end of the compression spring 40 may be attached to any location inside the applicator body 20.

Unless the cap 30 is pressed toward the bottom portion with a certain or greater force, the cap 30 is in a state of being located away from the bottom portion due to the elastic force of the compression spring 40. In the present embodiment, a state in which external force has been applied to the cap 30 and the cap 30 has been moved toward the bottom portion is called "pressed state". A state in which the cap 30 is not moved toward the bottom portion (a state in which the cap 30 is apart from the bottom portion due to the elastic force of the compression spring 40) is called "non-pressed state". As for the application kit 1, it can be said that the pressed state is a state in which the cap 30 has been brought closer to the cartridge 2 and the non-pressed state is a state in which the cap 30 is apart from the cartridge 2. It can also be said that the non-pressed state is a natural state for the applicator 3 and the cap 30. The structure or elastic force of the compression spring 40 may be designed such that a certain or greater pressing force is applied to the sheet member when the microneedle sheet 90 is applied to skin from the cartridge 2.

To both ends of the bottom portion of the applicator body 20 in the width direction, a pair of applicator-side connectors 22 configured to be detachably connected to the cartridge 2 is provided. Each applicator-side connector 22 has a box shape the lower side of which is open so as to receive the fitting portion 16 of the corresponding cartridge-side connector 12. On an outer wall of the applicator-side connector 22 in the width direction, a claw receiver 22a is formed in which the claw 18 of the cartridge-side connector 12 is to be engaged. In the present embodiment, this claw receiver 22a is a through hole.

The bottom portion of the applicator body 20 is provided with a pressing plate 23 extending in the width direction. When viewed along the front-and-rear direction, the pressing plate 23 is positioned near the bending portion 14 of the cartridge 2 that is attached to the applicator 3.

More specifically, the pressing plate 23 is positioned apart from the bending portion 14 by a small distance through which the microneedle sheet 90 can be narrowly passed. The pressing plate 23 has a bottom surface that is positioned at the same or substantially the same height as the lower surface of the support plate 11 of the cartridge 2 attached to the applicator 3 is. Slightly above the bottom surface of the pressing plate 23, a liner discharge port 23a extending along the front-and-rear direction is formed. The liner discharge port 23a is a through hole extending in the front-and-rear direction of the pressing plate 23, and plays a role in discharging the release liner of the microneedle sheet 90 that has been peeled from the sheet body 91 at the bending portion 14. Thus, the width of the liner discharge port 23a is set larger than the width of the release liner.

The applicator body 20 houses a stopper 50, a camshaft 60, and a resistance portion 70. The stopper 50 is a mechanical element configured to press the microneedle sheet 90 on the cartridge 2 to stop the microneedle sheet 90 from advancing. The camshaft 60 is a mechanical element for controlling the stopper 50. The resistance portion 70 is a mechanism configured to apply resistance to the microneedle sheet 90 that is advancing on the cartridge 2. Both the stopper 50 and the resistance portion 70 are provided to the bottom portion, and the stopper 50 is positioned posteriorly to the resistance portion 70.

The stopper 50 is formed with a plate member extending along the height direction and the width direction. The lower end of the stopper 50 has a linear shape extending along the width direction, and this lower end is brought into contact with the microneedle sheet 90 on the cartridge 2. The upper end of the stopper 50 is formed in an L-shape so as to be bent inside the applicator body 20.

The stopper 50 is attached inside the applicator body 20 with a compression spring 41 extending along the height direction. One end of the compression spring 41 is attached to the upper surface of the stopper 50, and the other end thereof is attached to the ceiling of the applicator body 20. The compression spring 41 applies elastic force acting in a direction toward the bottom portion to the stopper 50. Thus, in the non-pressed state, the stopper 50 is brought closer to the bottom portion by the elastic force of the compression spring 41. The compression spring 41 is one example of an elastic member for controlling the stopper 50. In the present embodiment, the compression spring 41 is a linear coil spring. However, the type of the compression spring is not limited to this, and a nonlinear coil spring, for example, may be used instead.

When the cartridge 2 is attached to the applicator 3, the stopper 50 is pressed against the microneedle sheet 90 on the support plate 11 of the cartridge 2 in the non-pressed state. Thus, in the non-pressed state, the microneedle sheet 90 is firmly nipped by the support plate 11 and the stopper 50, whereby the microneedle sheet 90 is stopped from advancing to the bending portion 14. The expression "to be stopped from advancing" herein means a state in which the microneedle sheet 90 (sheet member) cannot be caused to advance to the bending portion 14 unless the microneedle sheet 90 (sheet member) is forcefully pulled. The structure or elastic force of the compression spring 41 may be designed such that pressing force substantially sufficient to prevent the microneedle sheet 90 (sheet member) from unintentionally advancing in the non-pressed state is applied to the microneedle sheet 90 (sheet member).

The camshaft 60 is a rod-like member that is provided so as to be extending along the width direction of the applicator body 20. The camshaft 60 includes a first cam 62 formed on an outer peripheral surface of a rotating shaft 61 and a second cam 63 formed on the outer peripheral surface of the rotating shaft 61 and separated from the first cam 62 by about 180 degrees. The first cam 62 is fitted into a notch 32 formed in an inner wall of the cap 30. The second cam 63 is positioned below the L-shaped upper end of the stopper 50. In the present embodiment, both the first cam 62 and the second cam 63 are claws protruding in the radial direction of the camshaft 60. However, if they can function as cams, the specific shapes of the first cam 62 and the second cam 63 are not limited to particular ones.

The camshaft 60 operates when the cap 30 is pushed toward the bottom portion. In the non-pressed state, the second cam 63 is positioned below the upper end of the stopper 50 pressed against the bottom portion. When the user presses the cap 30 and the cap 30 is accordingly moved toward the bottom portion against elastic force of the compression spring 40 (i.e., when the applicator 3 is set into the pressed state), the upper end of the notch 32 comes into contact with the first cam 62 to push down the first cam 62. Accordingly, the camshaft 60 is rotated, and the second cam 63 positioned on the opposite side of the first cam 62 is moved upward along the circumferential direction to move the stopper 50 upward. By this movement of the second cam 63, the stopper 50 is pulled up against the elastic force of the compression spring 41. In other words, the stopper 50 is moved in the direction away from the bottom portion. When the user stops pressing the cap 30 and the cap 30 is accordingly moved in the direction away from the bottom portion by the elastic force of the compression spring 40 (i.e., when the applicator 3 returns to the non-pressed state), pushing down of the first cam 62 by the notch 32 is released. Accordingly, the camshaft 60 is rotated reversely, whereby the second cam 63 is moved downward along the circumferential direction. Consequently, the stopper 50 is moved toward the bottom portion by the elastic force of the compression spring 41.

The resistance portion 70 includes a roller 71 extending along the width direction, a compression spring 72 disposed so as to extend in the height direction above the roller 71, and a transmission portion 73 extending along the width direction and configured to transmit elastic force of the compression spring 72 to the roller 71. One end of the compression spring 72 is attached to an upper surface of the transmission portion 73, and the other end thereof is attached to a partition plate (not illustrated) formed on a central portion inside the applicator body 20 in the height direction. In the present embodiment, the compression spring 72 is a linear coil spring. However, the type of the compression spring is not limited to this, and a nonlinear coil spring, for example, may be used instead. When the cartridge 2 is attached to the applicator 3, the elastic force of the compression spring 72 is transmitted via the transmission portion 73 to the roller 71, whereby the roller 71 is pressed against the microneedle sheet 90 on the cartridge 2. In other words, the compression spring 72 provides elastic force for pressing the roller 71 against the microneedle sheet 90.

The roller 71 is one example of a pressing member. The roller 71 may be rotatably provided in order to smoothly deliver the microneedle sheet 90 while applying resistance such as rolling friction and sliding friction to the microneedle sheet 90 on the cartridge 2. However, rotation of the roller 71 is not indispensable. Because the roller 71 is pressed against the support plate 11 by the elastic force of the compression spring 72, the microneedle sheet 90 is nipped by the support plate 11 and the roller 71. The microneedle sheet 90 is nipped by using the elastic force in this manner, and thus the resistance applied to the microneedle sheet 90 can be kept constant.

If the elastic force of the compression spring 72 is excessively strong, it is difficult to cause the microneedle sheet 90 on the cartridge 2 to advance. If the elastic force is too weak, the microneedle sheet 90 on the cartridge 2 may go slack, and accordingly a situation may occur in which the microneedle sheet 90 cannot be appropriately applied to skin (e.g., a situation may occur in which the microneedles 92 cannot be raised sufficiently). The structure or elastic force of the compression spring 72 may be designed so that the microneedle sheet 90 can be stretched without slack and the user can appropriately operate the application kit 1.

Material for forming the applicator 3 and the cartridge 2 is not limited to a particular one. For example, the material may be plastic such as acrylic, may be metal, or may be another type of resin, for example, and these may be used in combination.

The dimensions of the application kit 1 (dimensions of the applicator 3 and the cartridge 2) may be determined based on any requirements. For example, the width of the application kit 1 may be determined based on the width of the microneedle sheet 90. The height and the entire length (length along the front-and-rear direction) of the application kit 1 may be determined in consideration of its operability.

[Method for Using Application Kit]

Figure 11:
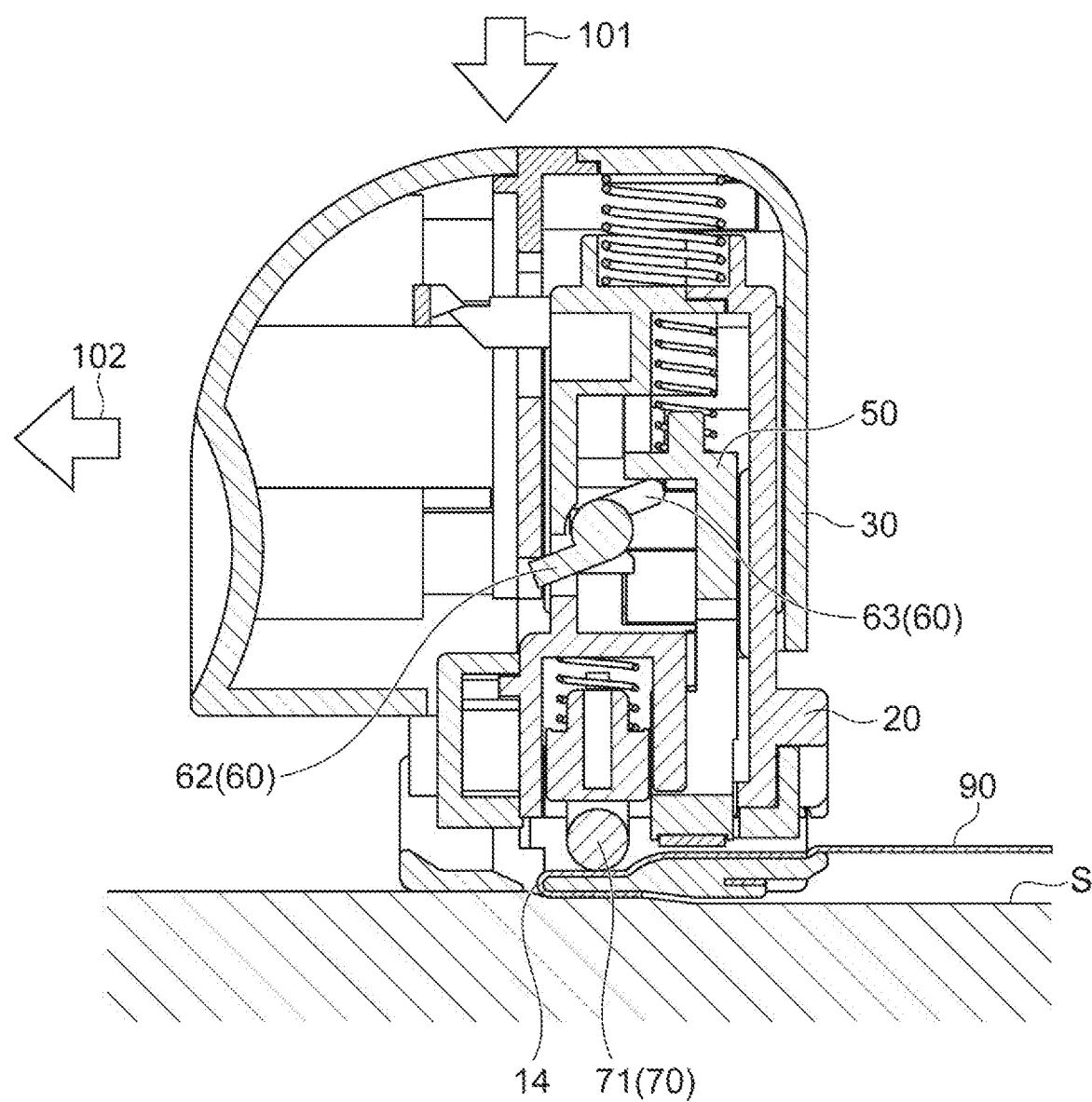
FIG. 11 is a sectional view for describing a method for using the application kit according to the embodiment.
Figure 12:
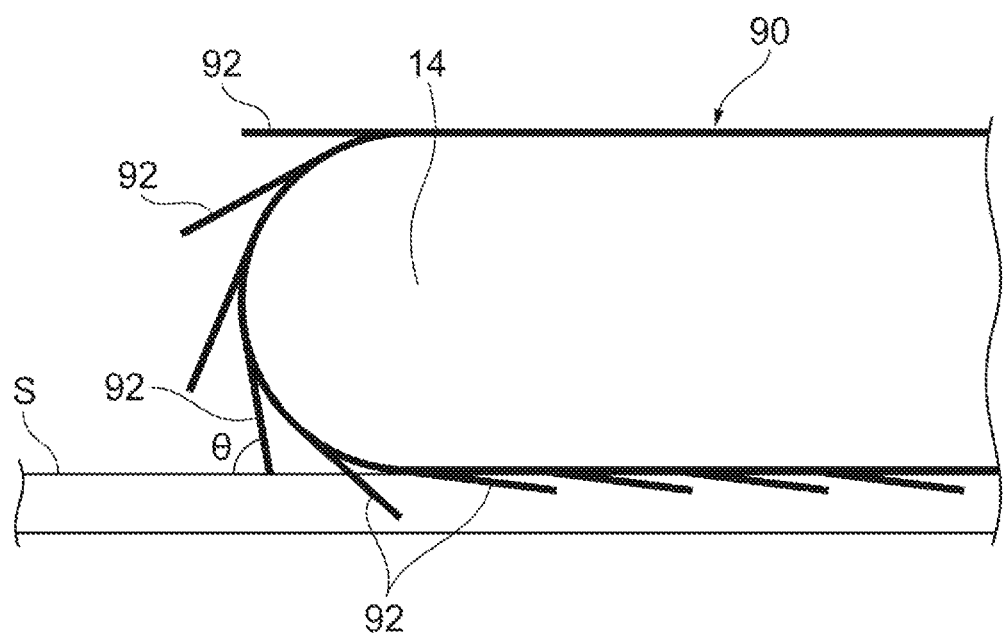
FIG. 12 is a diagram schematically illustrating a mode of puncture.

Referring to FIG. 11 and FIG. 12, the following describes a method for using the application kit 1. FIG. 11 is a sectional view for describing the method for using the application kit 1. FIG. 12 is a diagram schematically illustrating a mode of puncture.

To begin with, the user inserts the cartridge-side connectors 12 into the applicator-side connectors 22 to attach the cartridge 2 to the applicator 3. By this insertion, the claws 18 of the cartridge-side connectors 12 are hooked on the claw receivers 22a of the applicator-side connectors 22, whereby the applicator 3 and the cartridge 2 are integrated into the application kit 1. The tips of the microneedles 92 positioned on the upper surface of the support plate 11 of the cartridge 2 are oriented toward the bending portion 14 (i.e., forward).

Subsequently, the user puts the applicator 3 on skin S (more specifically, in an area where an active ingredient is to be applied). When the applicator 3 has been simply put on the skin S, the applicator 3 is in the non-pressed state (natural state). In this non-pressed state, the stopper 50 is pressed against the microneedle sheet 90 of the cartridge 2 by the compression spring 41, and the microneedle sheet 90 is firmly nipped by the stopper 50 and the support plate 11. Thus, the microneedle sheet 90 is stopped from advancing to the bending portion 14. The microneedle sheet 90 is also nipped by the support plate 11 and the roller 71.

Herein, in order to prevent the microneedle sheet 90 from being displaced on the skin S due to the subsequent operation of the applicator 3, adhesive may be applied to one end of the microneedle sheet 90 (end portion thereof that is brought into contact with the skin S from the beginning).

As illustrated in FIG. 11, while pushing the cap 30 toward the applicator body 20 along the height direction, the user moves the applicator 3 such that the microneedle sheet 90 is drawn into the cartridge body 10. In other words, the user moves the applicator 3 forward (see the arrow 102) while pushing the cap 30 from substantially right above the skin S (see the arrow 101).

When the cap 30 is pushed, the notch 32 pushes the first cam 62 toward the bottom portion, whereby the first cam 62 is lowered along the circumferential direction. Accordingly, the camshaft 60 is rotated, whereby the second cam 63 is raised along the circumferential direction. Consequently, the stopper 50 engaging with the second cam 63 is also raised, and thus a clearance is formed between the stopper 50 and the support plate 11. Because the stopper 50 is raised in this manner in the pressed state, during a period when the user is moving the applicator 3 forward while pushing the cap 30, the microneedle sheet 90 advances on the support plate 11 without being stopped by the stopper 50. The microneedle sheet 90 passes through the resistance portion 70 (more specifically, the roller 71) to reach the bending portion 14. Until having reached the bending portion 14, the microneedles 92 are in the state of lying along the main surface 91a.

The compression spring 72 presses the roller 71 against the support plate 11 continuously even when the cap 30 is pushed and the stopper 50 is accordingly raised. Thus, also during a period when the applicator 3 is being moved forward in the pressed state, the resistance portion 70 applies resistance to the microneedle sheet 90 advancing to the bending portion 14. Consequently, tension is applied to the microneedle sheet 90, whereby the microneedle sheet 90 is guided to the bending portion 14 without slack to be applied to the skin S.

The microneedle sheet 90 that has advanced in the pressed state is bent (turned around) at the bending portion 14 by about 180 degrees. Accordingly, as depicted in FIG. 12, microneedles 92 located in a bent portion are raised from the main surface 91a, and the raised microneedles 92 are inserted into the skin S. The microneedles 92 that are raised between the applicator 3 and the skin S at once are those in one row along the width direction of the microneedle sheet 90. The bending portion 14 widens the angle formed between each microneedle 92 and the main surface 91a, and this widened angle is larger than 0 degrees and smaller than 180 degrees as a matter of course. As depicted in FIG. 12, the puncture angle θ (angle formed between the microneedle 92 and the skin S) when the microneedle 92 raised from the main surface 91a is inserted into the skin S is also larger than 0 degrees and smaller than 180 degrees. The lower limit of the puncture angle may be 20 degrees, 34 degrees, or 40 degrees, and the upper limit of the angle may be 160 degrees, 140 degrees, or 100 degrees. If the skin S can be punctured with the microneedles 92, the angle by which the microneedle sheet 90 is bent at the bending portion 14 is not limited to 180 degrees. For example, this angle may be within a range of 135 to 180 degrees, and more specifically, may be 135 degrees, 150 degrees, 165 degrees, or 175 degrees.

During a period when the user is moving the application kit 1 on the skin S, the pressing plate 23 is in contact with the skin S, and the skin S is pulled by the pressing plate 23. Consequently, part of the skin S to which the microneedles 92 are to be applied is stretched by the pressing plate 23, which allows the skin S to be easily punctured with the microneedles 92 raised by the bending portion 14. In other words, the pressing plate 23 enables more reliable puncture with the microneedles 92.

When the user moves the application kit 1 by a desired distance, a plurality of microneedles 92 located in a range of this distance are inserted into the skin S. Thus, the user can administer a desired amount of an active ingredient by adjusting the application area of the microneedle sheet 90. The user may remove the microneedle sheet 90 soon, or may apply the microneedle sheet 90 to the skin S continuously for a predetermined period of time. After having applied the microneedle sheet 90 to the skin S, the user can easily remove the cartridge 2 from the applicator 3 by pulling the cartridge 2 downward while lightly pushing the handles 17 of the cartridge 2 inward in the width direction of the cartridge 2.

As described above, the application kit 1 can be used also for application of a patch. The patch is set in the cartridge 2 in advance with its adhesive layer facing upward. The user moves the application kit 1 forward while pushing the cap 30 toward the cartridge 2. By this operation, at the bending portion 14, the patch is bent such that the adhesive layer (active surface of the patch) faces outward of the arc of the bending portion, and the patch is stuck to the skin.

[Effects]

As described in the foregoing, an applicator according to one aspect of the present invention includes: an applicator body; an applicator-side connector provided to a bottom portion of the applicator body and configured to be detachably connected to a cartridge including a bending portion configured to bend a sheet member for applying the sheet member to skin; a cap provided above the applicator body and being movable along a height direction of the applicator body; and an elastic member extending along the height direction between the applicator body and the cap and configured to apply, to the cap, an elastic force that acts in a direction away from the bottom portion. In a pressed state in which the applicator-side connector has been connected to the cartridge and the cap has been moved toward the bottom portion against the elastic force, the bending portion bends the sheet member that has advanced to the bending portion.

A cartridge according to one aspect of the present invention includes: a sheet member; a bending portion configured to bend the sheet member for applying the sheet member to skin; and a cartridge-side connector configured to be detachably connected to an applicator configured to apply a force toward the sheet member. In a pressed state in which the cartridge-side connector has been connected to the applicator and the applicator has applied the force to the cartridge, the bending portion bends the sheet member that has advanced to the bending portion.

An application kit according to one aspect of the present invention includes: a cartridge including a sheet member; and an applicator being connectable to the cartridge. The cartridge includes: a bending portion configured to bend the sheet member for applying the sheet member to skin; and a cartridge-side connector configured to be detachably connected to the applicator. The applicator includes: an applicator body; an applicator-side connector provided to a bottom portion of the applicator body; a cap provided above the applicator body and being movable along a height direction of the applicator body; and an elastic member extending along the height direction between the applicator body and the cap and configured to apply, to the cap, an elastic force that acts in a direction away from the bottom portion. In a pressed state in which the cartridge-side connector has been connected to the applicator-side connector and the cap has been moved toward the bottom portion against the elastic force, the bending portion bends the sheet member that has advanced to the bending portion.

In this aspect, the sheet member is bent by the bending portion and is applied to the skin in the pressed state in which the applicator has been connected to the cartridge and the cap has been moved toward the bottom portion. By this mechanism, whoever uses this applicator, the sheet member is applied to the skin with a certain or greater pressing force being applied to the sheet member from the applicator via the cartridge. Because the pressing force applied to the sheet member is maintained at a certain or greater level during the application, variations in application of the sheet member to the skin can be reduced. For example, when the sheet member is a patch, anyone who uses this application kit can securely apply an adhesive layer thereof to his/her skin while preventing the patch from wrinkling When the sheet member is a microneedle sheet, anyone who uses this application kit can raise microneedles thereof from a main surface of the sheet, thereby securely inserting the microneedles into his/her skin.

Furthermore, the cartridge to which the sheet member is attached in advance is prepared as a tool that is separate from the applicator. Thus, the user can easily attach the sheet member to the applicator by simply connecting the cartridge to the applicator, without complicated operation of attaching the sheet member itself to the applicator.

In the applicator according to another aspect, the applicator body may further include: a stopper configured to press the sheet member on the cartridge in a non-pressed state in which the cap is apart from the bottom portion due to the elastic force, and be moved away from the sheet member in the pressed state; and a camshaft configured to move the stopper toward the sheet member when the cap is moved in the direction away from the bottom portion by the elastic force, and move the stopper in a direction away from the sheet member when the cap is moved toward the bottom portion against the elastic force.

In the application kit according to another aspect, the applicator body may further include: a stopper configured to press the sheet member on the cartridge in a non-pressed state in which the cap is apart from the bottom portion due to the elastic force, and be moved away from the sheet member in the pressed state; and a camshaft configured to move the stopper toward the sheet member when the cap is moved in the direction away from the bottom portion by the elastic force, and move the stopper in a direction away from the sheet member when the cap is moved toward the bottom portion against the elastic force.

In these aspects, because the sheet member does not advance unless the cap is moved toward the bottom portion (i.e., unless the applicator is operated), the sheet member can be prevented from unintentionally advancing.

In the applicator according to another aspect, the applicator body may further include a resistance portion configured to apply resistance to the sheet member on the cartridge.

In the application kit according to another aspect, the applicator body may further include a resistance portion configured to apply resistance to the sheet member on the cartridge.

In these aspects, because tension is applied to the sheet member by applying the resistance to the sheet member that is advancing, the sheet member advances without slack, and consequently, the sheet member can be applied to the skin with constant force.

The applicator according to another aspect may further include a pressing plate positioned near the cartridge connected to the applicator-side connector, and the pressing plate may have a bottom surface that is positioned at substantially the same height as a lower surface of the cartridge connected to the applicator-side connector is.

In the application kit according to another aspect, the applicator may further include a pressing plate positioned near the cartridge connected to the applicator-side connector, and the pressing plate may have a bottom surface that is positioned at substantially the same height as a lower surface of the cartridge connected to the applicator-side connector is.

In these aspects, because part of the skin to which the sheet member is to be applied is stretched by this pressing plate, the sheet member can be securely applied to the skin.

In the applicator according to another aspect, the applicator-side connector may be a pair of connectors provided to both ends of the bottom portion in a width direction thereof. By configuring the cartridge-side connector in this manner, the cartridge can be more reliably attached to the applicator.

The cartridge according to another aspect may further include a support plate configured to support the sheet member, and the bending portion may be one linear end of the support plate.

In the application kit according to another aspect, the cartridge may further include a support plate configured to support the sheet member, and the bending portion may be one linear end of the support plate.

In these aspects, because causing the one end of the support plate to serve as the bending portion eliminates the need to separately prepare a component configured to bend the sheet member, the structure of the cartridge can be simplified.

In the cartridge according to another aspect, the cartridge-side connector may be a pair of connectors provided to both ends of the support plate in a width direction thereof. By configuring the cartridge-side connector in this manner, the cartridge can be more reliably attached to the applicator.

[Modification]

The present invention has been described above in detail based on the embodiment. However, the present invention is not limited to the embodiment above. In the present invention, various modifications may be made without departing from the gist thereof.

In the embodiment, springs have been described as elastic members. However, the elastic members are not limited to the springs. For example, part or all of each elastic member used as a component of the applicator may be an elastic body (e.g., rubber) other than a spring.

In the embodiment, the microneedle sheet 90 is fixed to the cartridge body 10 with the through hole 93 of the microneedle sheet 90 and the claw 15 of the cartridge body 10. However, the fixing method is not limited to this. For example, thin magnets may be provided to the first end of the microneedle sheet 90 in the longitudinal direction and the lower surface of the support plate 11 of the cartridge body 10, and the microneedle sheet 90 may be fixed to the cartridge body 10 with both magnets.

The stopper configured to stop the sheet member from advancing, the camshaft for controlling the stopper, and the resistance portion configured to apply resistance to the sheet member may all be omitted.

As described above, the sheet member is not limited to a microneedle sheet. The application kit according to each aspect of the present invention may be used for other types of sheet members including a patch.

In the embodiment, the cartridge-side connectors 12 and the applicator-side connectors 22 are each a pair of connectors. However, the shape of connectors for connecting the cartridge to the applicator is not limited to this. For example, one of a cartridge-side connector and an applicator-side connector may have one protruding structure, and the other thereof may have one recessed structure corresponding to the protruding shape.

Figure 13:
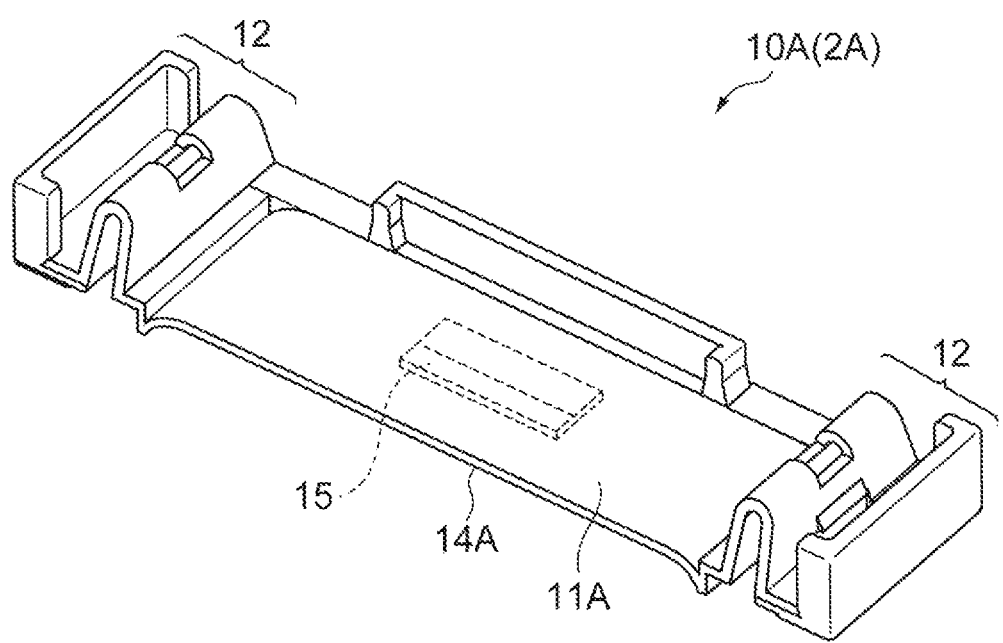
FIG. 13 is a perspective view of a cartridge according to a modification when viewed from above.

Referring to FIG. 13, the following describes a cartridge 2A as one modification of the cartridge. FIG. 13 is a perspective view of the cartridge 2A according to the modification when viewed from above. The cartridge 2A includes a microneedle sheet 90 (sheet member) and a cartridge body 10A configured to support the microneedle sheet 90. The microneedle sheet 90 is attached to the cartridge body 10A, whereby the cartridge 2A is formed. In FIG. 13, the microneedle sheet 90 is omitted. The cartridge 2A is partially different in structure from the cartridge 2. The following describes portions different from those of the cartridge 2 in particular.

The cartridge body 10A is a small component having a structure corresponding to the bottom portion of the applicator 3 (more specifically, the bottom portion of the applicator body 20). The cartridge body 10A includes a support plate 11A and a pair of cartridge-side connectors 12. Although the structure of the support plate 11A is different from that of the support plate 11, the structure of the pair of cartridge-side connectors 12 is the same as that in the case of the cartridge 2.

The support plate 11A is a rectangular plate configured to support at least part of the microneedle sheet 90. The width of an upper surface of the support plate 11A is set according to the width of the microneedle sheet 90, and this setting allows the microneedle sheet 90 before being applied to skin to advance straight forward without wobbling. The support plate 11A is different from the support plate 11 of the cartridge 2 in being formed so as to protrude upward (i.e., toward the applicator 3). For example, at least part of the support plate 11A is curved, whereby this protruding shape is formed. In FIG. 13, both ends of the support plate 11A in the width direction are curved, and a central portion thereof has a planar shape. However, the protruding shape of the support plate is not limited to this and, for example, the protruding shape may be formed by curving the whole of the support plate. By using this protruding shape, the shape of the support plate becomes closer to the shape of a living body, and thus adhesion between the skin and the sheet member (e.g., the microneedle sheet 90) can be further increased.

The cartridge body 10A includes a bending portion 14A configured to bend the microneedle sheet 90 that has advanced to the bending portion 14A to apply the microneedle sheet 90 to skin. When the cartridge body 10A is viewed along the vertical direction, the bending portion 14A has a linear shape. When the cartridge body 10A is viewed along the front-and-rear direction, at least part of the bending portion 14A has a curved shape corresponding to the protruding shape of the support plate 11A. In this modification, the bending portion 14A is a front end (an edge on the front side; this edge looks straight when the cartridge body 10A is viewed along the vertical direction) of the support plate 11A. However, the specific shape or structure of the bending portion 14A is not limited to a particular one. For example, the bending portion 14A may be formed so as to include an elongated columnar member.

On a lower surface of the support plate 11A, a claw 15 for fixing a first end of the microneedle sheet 90 in the longitudinal direction to the cartridge 2 is formed. The structure of the claw 15 is the same as that in the case of the cartridge 2. The microneedle sheet 90 is attached to the cartridge body 10A in advance by placing the first end of the microneedle sheet 90 onto the upper surface of the support plate 11A, pulling out the first end to the bending portion 14A, bending the microneedle sheet 90 with the bending portion 14A, and hooking, on the claw 15, the through hole 93 that has been moved to the lower surface of the support plate 11A. This attaching method is also the same as that in the case of the cartridge 2.

As described above, in the cartridge according to another aspect, the support plate may be formed so as to protrude toward the applicator. By this protruding shape, adhesion between the skin and the sheet member can be further increased.

REFERENCE SIGNS LIST

1 . . . application kit, 2, 2A . . . cartridge, 3 . . . applicator, 10, 10A . . . cartridge body, 11, 11A . . . support plate, 12 . . . cartridge-side connector, 13 . . . guide, 14, 14A . . . bending portion, 15 . . . claw, 20 . . . applicator body, 22 . . . applicator-side connector, 23 . . . pressing plate, 30 . . . cap, 50 . . . stopper, 60 . . . camshaft, 62 . . . first cam, 63 . . . second cam, 70 . . . resistance portion, 90 . . . sheet, 91 . . . sheet body, 91a . . . main surface, 92 . . . microneedle, 93 . . . through hole.

The invention claimed is:

1. An applicator comprising:
an applicator body;
an applicator-side connector provided to a bottom portion of the applicator body and configured to be detachably connected to a cartridge including a bending portion configured to bend a sheet member for applying the sheet member to skin;
a cap provided above the applicator body and being movable along a height direction of the applicator body; and
an elastic member extending along the height direction between the applicator body and the cap and configured to apply, to the cap, an elastic force that acts in a direction away from the bottom portion, wherein
in a pressed state in which the applicator-side connector has been connected to the cartridge and the cap has been moved toward the bottom portion against the elastic force, the bending portion bends the sheet member that has advanced to the bending portion.

2. The applicator according to claim 1, wherein
the applicator body further includes:
a stopper configured to press the sheet member on the cartridge in a non-pressed state in which the cap is apart from the bottom portion due to the elastic force, and be moved away from the sheet member in the pressed state; and
a camshaft configured to move the stopper toward the sheet member when the cap is moved in the direction away from the bottom portion by the elastic force, and move the stopper in a direction away from the sheet member when the cap is moved toward the bottom portion against the elastic force.

3. The applicator according to claim 1, wherein
the applicator body further includes a resistance portion configured to apply resistance to the sheet member on the cartridge.

4. The applicator according to claim 1, further comprising a pressing plate positioned near the cartridge connected to the applicator-side connector, wherein
the pressing plate has a bottom surface that is positioned at substantially the same height as a lower surface of the cartridge connected to the applicator-side connector.

5. The applicator according to claim 1, wherein the applicator-side connector is a pair of connectors provided to both ends of the bottom portion in a width direction thereof.

6. A cartridge comprising:
a sheet member;
a bending portion configured to bend the sheet member for applying the sheet member to skin;
a cartridge-side connector configured to be detachably connected to an applicator configured to apply a force toward the sheet member; and
a support plate configured to support the sheet member, wherein
in a pressed state in which the cartridge-side connector has been connected to the applicator and the applicator has applied the force to the cartridge, the bending portion bends the sheet member that has advanced to the bending portion, and
the bending portion is one linear end of the support plate.

7. The cartridge according to claim 6, wherein the cartridge-side connector is a pair of connectors provided to both ends of the support plate in a width direction thereof.

8. The cartridge according to claim 6, wherein the support plate is formed so as to protrude toward the applicator.

9. An application kit comprising:
a cartridge including a sheet member; and
an applicator being connectable to the cartridge, wherein
the cartridge includes:
 a bending portion configured to bend the sheet member for applying the sheet member to skin; and
 a cartridge-side connector configured to be detachably connected to the applicator,
the applicator includes:
 an applicator body;
 an applicator-side connector provided to a bottom portion of the applicator body;
 a cap provided above the applicator body and being movable along a height direction of the applicator body; and
 an elastic member extending along the height direction between the applicator body and the cap and configured to apply, to the cap, an elastic force that acts in a direction away from the bottom portion, and
in a pressed state in which the cartridge-side connector has been connected to the applicator-side connector and the cap has been moved toward the bottom portion against the elastic force, the bending portion bends the sheet member that has advanced to the bending portion.

10. The application kit according to claim 9, wherein the applicator body further includes:
 a stopper configured to press the sheet member on the cartridge in a non-pressed state in which the cap is apart from the bottom portion due to the elastic force, and be moved away from the sheet member in the pressed state; and
 a camshaft configured to move the stopper toward the sheet member when the cap is moved in the direction away from the bottom portion by the elastic force, and move the stopper in a direction away from the sheet member when the cap is moved toward the bottom portion against the elastic force.

11. The application kit according to claim 9, wherein the applicator body further includes a resistance portion configured to apply resistance to the sheet member on the cartridge.

12. The application kit according to claim 9, wherein the applicator further includes a pressing plate positioned near the cartridge connected to the applicator-side connector, and
the pressing plate has a bottom surface that is positioned at substantially the same height as a lower surface of the cartridge connected to the applicator-side connector.

13. The application kit according to claim 9, wherein the cartridge further includes a support plate configured to support the sheet member, and
the bending portion is one linear end of the support plate.

\* \* \* \* \*